United States Patent
Van Es et al.

(10) Patent No.: US 11,602,215 B2
(45) Date of Patent: Mar. 14, 2023

(54) SKIN TREATMENT DEVICE WITH DIFFERENT SKIN TREATMENT SURFACES

(71) Applicant: KONINKLIJKE PHILIPS N.V., Eindhoven (NL)

(72) Inventors: Michel Van Es, Drachten (NL); Thibault Paul Faucon, Drachten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 975 days.

(21) Appl. No.: 16/348,729

(22) PCT Filed: Nov. 7, 2017

(86) PCT No.: PCT/EP2017/078375
§ 371 (c)(1),
(2) Date: May 9, 2019

(87) PCT Pub. No.: WO2018/087051
PCT Pub. Date: May 17, 2018

(65) Prior Publication Data
US 2019/0320784 A1 Oct. 24, 2019

(30) Foreign Application Priority Data

Nov. 11, 2016 (EP) .................................. 16198521
Nov. 25, 2016 (EP) .................................. 16200818

(51) Int. Cl.
*A46B 13/02* (2006.01)
*A61B 90/80* (2016.01)
(Continued)

(52) U.S. Cl.
CPC ............ *A46B 13/02* (2013.01); *A46B 5/0095* (2013.01); *A46B 13/008* (2013.01); *A61B 17/54* (2013.01);
(Continued)

(58) Field of Classification Search
CPC ......... A46B 7/06; A46B 13/00; A46B 13/001; A46B 13/02; A46B 13/023; A46B 13/008;
(Continued)

(56) References Cited

U.S. PATENT DOCUMENTS

| 8,261,395 B2 * | 9/2012 | Lazarre .................. A46B 13/02 15/97.1 |
| 2003/0125754 A1 | 7/2003 | Davis |
| 2004/0097967 A1 | 5/2004 | Ignon |
| 2014/0330289 A1 * | 11/2014 | Revivo .................. A46B 13/02 606/131 |

(Continued)

FOREIGN PATENT DOCUMENTS

| CN | 203280707 U | 11/2013 |
| JP | 2001333817 A | 12/2001 |

(Continued)

*Primary Examiner* — Robert J Scruggs (57) ABSTRACT

The invention relates to a skin treatment device comprising a housing (10) with a handle section (11), a disc-shaped skin treatment element (21), a drive mechanism incorporated in said housing and coupled to said skin treatment element for driving said skin treatment element into rotational movement about a rotational axis, wherein said skin treatment element has a first skin treatment surface (22) and a second skin treatment surface (25), said first skin treatment surface (22) being oriented axially with respect to said rotational axis, said second skin treatment surface (25) being oriented radially with respect to said rotational axis and extending along a circumference of the skin treatment element.

16 Claims, 3 Drawing Sheets

(51) Int. Cl.
   *A46B 5/00*       (2006.01)
   *A46B 13/00*      (2006.01)
   *A61B 17/54*      (2006.01)
   *A61H 7/00*       (2006.01)
   *A61B 17/00*      (2006.01)

(52) U.S. Cl.
   CPC .............. *A61B 90/80* (2016.02); *A61H 7/005* (2013.01); *A46B 2200/102* (2013.01); *A61B 2017/00761* (2013.01); *A61H 2201/1215* (2013.01); *A61H 2201/1692* (2013.01)

(58) Field of Classification Search
   CPC .................. A46B 15/00; A46B 5/0095; A46B 2200/102; A61B 90/80; A61B 17/54; A61B 2017/00761; A61H 7/005; A61H 2201/1215; A61H 2201/1692; A45D 29/05; A45D 29/14; A47K 7/043
   See application file for complete search history.

(56) References Cited

U.S. PATENT DOCUMENTS

| | | | |
|---|---|---|---|
| 2015/0150352 A1* | 6/2015 | Yiu | A45D 29/05 132/75.8 |
| 2015/0182078 A1* | 7/2015 | Miller | A46B 13/04 15/104.93 |
| 2016/0045081 A1* | 2/2016 | Kern | A46B 13/008 15/22.4 |
| 2017/0112333 A1* | 4/2017 | McCauley | A46B 13/008 |

FOREIGN PATENT DOCUMENTS

| | | |
|---|---|---|
| RU | 139889 U1 | 4/2014 |
| WO | 33022175 A2 | 3/2003 |
| WO | 2006031413 A2 | 3/2006 |
| WO | 2009148729 A2 | 12/2009 |
| WO | 2013096520 A1 | 6/2013 |
| WO | 2014078444 A1 | 5/2014 |

* cited by examiner

FIG. 3

SKIN TREATMENT DEVICE WITH DIFFERENT SKIN TREATMENT SURFACES

This application is the U.S. National Phase application under 35 U.S.C. § 371 of International Application No. PCT/EP2017/078375, filed on Nov. 7, 2017 and International Application No. 16198521.3, filed Nov. 11, 2016 and International Application No. 16200818.9 filed Nov. 25, 2016. These applications are hereby incorporated by reference herein.

FIELD OF THE INVENTION

The invention relates to a skin treatment device having a disc-shaped skin treatment element mounted to a housing and configured for rotational movement.

BACKGROUND OF THE INVENTION

Skin treatment devices as described hereinbefore are generally used for treatments of the skin like abrading callus, massaging, enhancing the application of creams, fluids or other compounds, removing contaminations, impurities or cosmetics.

WO 2009/148729 discloses an instrument for pedicure with a rotary abrasive attachment serving to effectuate the removal of skin imperfections. The rotary abrasive attachment is removably secured to a wheel and is formed like a cap with abrasive material covering a distal surface and an outer surface of a rim of said cap. While such instrument may be useful in some applications for skin treatment, a problem arises from the fact that the abrasive material is present on a circumferential surface and on an axial surface of the cap and, thus, different velocities of the abrasive surface areas will occur. This may produce injuries like burning due to inadequate adjustment of the rotational speed when using the different surface areas of the cap. A further drawback of an instrument designed according to this prior art is inefficient treatment by some areas of the abrasive cap due to a not properly adjusted velocity of the abrasive surface in some areas of the cap. Similar devices are known from JP 2001 333 817 A and CN 203280707 U.

US 2015/0150352 discloses another cosmetic device. This cosmetic device is equipped with a drum assembly. According to one embodiment, only the circumferential surface of such a drum assembly is coated with abrasive material and, thus, the problem of different velocities of the abrasive material in different regions of the drum is overcome. Further, an embodiment according to this prior art comprises two adjacent abrasive sections on such a circumferential drum surface with different portions that provide different characteristics like abrasiveness, shape, compressibility. While the disclosed apparatus may be used for variable skin treatments, the geometry of the tool is somewhat difficult to handle and is not well suited for specific applications when treating small skin regions.

US 2016/0045081 discloses a cleansing device for human skin including a rotating cleansing head having a plurality of elastomeric cleansing features extending away from a surface of the cleansing head. In an embodiment, the cleansing head comprises a three-dimensional frustoconical shape. In this embodiment, a first section of the cleansing head is provided on a flat top surface of the cleansing head, a second section of the cleansing head is partially provided on the flat top surface and partially on a circumferential side surface of the cleansing head, and a third section of the cleansing head is provided on the circumferential side surface of the cleansing head. The three sections may counter-oscillate relative to each other. The arrangement of the three sections on different parts of the cleansing head may facilitate cleansing of hard-to reach areas of the face.

SUMMARY OF THE INVENTION

It is an object of the invention to provide a skin treatment device which allows various skin treatments without the risk of doing harm to the skin.

This problem is solved by a skin treatment device comprising a housing with a handle section, a disc-shaped skin treatment element, a drive mechanism incorporated in said housing and coupled to said skin treatment element for driving said skin treatment element into rotational movement about a rotational axis, wherein said skin treatment element has a first skin treatment surface and a second skin treatment surface, said first skin treatment surface being provided on a main side of the disc-shaped skin treatment element and having an average orientation perpendicular with respect to said rotational axis, said second skin treatment surface being oriented radially with respect to said rotational axis and extending along a circumference of the skin treatment element, wherein said first skin treatment surface is formed and intended to effect a skin treatment by a first surface characteristic and said second skin treatment surface is formed and intended to effect a skin treatment by a second surface characteristic, wherein said first surface characteristic and said second surface characteristic are adapted and intended to effect a skin treatment, and wherein said first surface characteristic is different from said second surface characteristic.

According to the invention, a disc-shaped skin treatment element forming a tool of the skin treatment device is employed and driven into rotational movement. The rotational movement may be unidirectional, i.e. it may be a continuous motion either in clockwise or anticlockwise direction. The direction of the movement may be switched from one direction to the other and vice versa. Further, the rotational movement may be a reciprocal movement.

The disc-shaped skin treatment element has a first skin treatment surface and a second skin treatment surface. The first skin treatment surface is provided on a main side of the disc-shaped skin treatment element, in particular a main side of the disc-shaped skin treatment element facing the skin of the user during use. The first skin treatment surface has an average orientation perpendicular with respect to the rotational axis. Accordingly, the whole first skin treatment surface or a part of this first skin treatment surface is oriented perpendicularly to an axial direction of the rotational axis, wherein the axial direction is understood to be parallel to the rotational axis of the disc. The first skin treatment surface may be planar, in which case the whole first skin treatment surface is oriented perpendicularly to the axis of rotation, or curved, like e.g. convex or concave shaped, in which case an average orientation of the curved first skin treatment surface is perpendicular to the axis of rotation. In particular this will be the case when the curved first skin treatment surface is rotationally symmetrical with respect to the axis of rotation, with a central portion of the first skin treatment surface intersected by the axis of rotation being perpendicular to the axis of rotation. The second skin treatment surface is oriented radially. This is understood to be an orientation wherein the second skin treatment surface lies perpendicularly to a vector having a radial component relative to the rotational axis, in particular a vector which is predominantly oriented radially relative to the rotational axis. The second skin treatment surface may be a circumferential or peripheral surface, like e.g. an outer peripheral surface of a cylinder, a conically shaped peripheral surface or a peripheral or circumferential surface having a curved shape in a longitudinal sectional view comprising the rotational axis. Like the first skin treatment surface, the second skin treatment surface may have a convex or concave shape in a longitudinal sectional view of the disc-shaped skin treatment element.

The second skin treatment surface extends along the circumference of the disk-shaped skin treatment element, and preferably extends over an angular range of 360° about the rotational axis along the circumference of the skin treatment element. As a result, a continuous rotational movement as well as a reciprocal movement may be used to conduct a treatment by means of said radially oriented second skin treatment surface. In some embodiments, the second skin treatment surface may comprise two, three, four or even more surface sections, each surface section extending along a part of the circumference only, wherein said surface sections have surface characteristics different from each other. These embodiments may be combined with a reciprocal rotational movement of the skin treatment element and, thus, may allow the selection of two or more different surface characteristics for the treatment of the skin.

The axial length of the second skin treatment surface in a direction parallel to the rotational axis is understood not to be limited by the definition of the skin treatment element being disc-shaped. In particular, skin treatment elements formed like an elongate cylinder having a second skin treatment surface with a significant axial length are understood to constitute also a disc-shaped skin treatment element.

The first skin treatment surface and the second skin treatment surface differ in their geometrical orientation and further differ in that different surface characteristics are provided at these skin treatment surfaces. Whilst the first skin treatment surface has a first surface characteristic formed and intended to effect a skin treatment by said first skin treatment surface, the second skin treatment surface has a second surface characteristic, formed and intended to effect a skin treatment by said second skin treatment surface, which is different from said first surface characteristic. This particular configuration allows to compensate for different velocities of the areas of the first and the second skin treatment surfaces and thus to prevent the skin from being harmed during the treatment. At the same time, this particular configuration effects an efficient skin treatment by both the first skin treatment surface and the second skin treatment surface at a constant number of revolutions per minute. As a further aspect and advantage of the invention, different surface characteristics are provided at the first and the second skin treatment surfaces, thus providing a variable use of the skin treatment device in that the user may either apply the first skin treatment surface to treat the skin or the second skin treatment surface for such skin treatment.

In a preferred embodiment, said first surface characteristic is adapted and intended to effect a first type of skin treatment and said second skin treatment surface is adapted and intended to effect a second type of skin treatment different from said first type of skin treatment. In this embodiment, different types of skin treatment are to be understood as skin treatments of different nature by applying different types of operations on the skin using different functional skin treatment systems, such as for example abrading and brushing, cleaning and massaging. This will allow, e.g., to provide a skin-abrading treatment with one of the first and second skin treatment surfaces and a skin-polishing treatment with the other one of the first and second skin treatment surfaces. Generally, the first and the second skin treatment surfaces may be designed to provide functions like abrading, polishing, massaging, brushing, cleaning and the like, and in particular the first and second skin treatment surfaces are different in such a way that two different functions are provided by the first and second skin treatment surfaces.

In another preferred embodiment, said first surface characteristic is adapted and intended to effect a first type of skin treatment at a first intensity and said second skin treatment surface is adapted and intended to effect said first type of skin treatment at a second intensity different from the said first intensity. In this embodiment, a single function is provided by the first and second skin treatment surfaces, wherein this single function is provided at different intensities by the first and second skin treatment surfaces such as, e.g., by providing different grit sizes for an abrasion treatment or different types of brush filaments for a brushing treatment.

It is noted that, according to the invention, the first and second surface characteristics are adapted and intended to effect a skin treatment, and that the first and second skin treatment surfaces are formed and intended to effect a skin treatment by, respectively, said first and second skin treatment surfaces. It is noted that, in this respect, the expression "intended to effect a skin treatment" is meant to indicate that the first and second treatment surfaces and the first and second surface characteristics are intentionally provided on the skin treatment device to intentionally perform a skin treatment, for example, when brought into contact with the skin. Thus, for example, a circumferential surface of a rotating disc-shaped skin treatment element, which is merely present as a naturally occurring part of the skin treatment element without having an intentional skin treatment function such as, for example, a smooth circumferential surface only having for example a decorative function, is not to be considered as a skin treatment surface which is formed and intended to effect a skin treatment by the presence of a surface characteristic which is adapted and intended to effect a skin treatment, despite the fact that such a naturally occurring part of the skin treatment element could for example be brought into contact with the skin.

According to a further preferred embodiment, said first surface characteristic and/or said second surface characteristic are selected from a brush tool, an abrasive tool with a first grit size, an abrasive tool with a second grit size being coarser than the first grit size, or a polishing tool.

According to this embodiment, the axially oriented first skin treatment surface may comprise a brush-type surface characteristic which may comprise a plurality of single bundles of bristles to effect a massaging, cleaning or polishing function or to intensify the effect of fluids, pastes or creams applied to the skin. Further, the first surface characteristic may be an abrasive tool, which is understood to be a surface structure like that of sand paper or other grinding materials. Generally, such an abrasive tool may have a first grit size or a second grit size which is coarser than the first grit size, wherein the first grit size may be understood to have an ANSI specification of 240 or more, whereas the second grit size may be understood to have an ANSI grit size of less than 240. Still further, the first surface characteristic may be adapted to effect a polishing treatment in that it is provided by, e.g., a foam-like material, a felt-like material, a textile material, a cotton wool or a wadding-type material.

The first skin treatment surface may in particular serve for the treatment of relatively large skin areas, which may be well accomplished by the axial orientation of the first skin treatment surface and its dimension and geometry.

The second skin treatment surface will usually have a geometry which provides a uniform or only slightly differing velocity of the second skin treatment surface over its entire area when the skin treatment element is rotated. This will allow to apply a second surface characteristic which is sensible to variations of the velocity and which preferably is to be used at a predetermined velocity only or in a predetermined velocity range only. The second surface characteristic may be selected from any such tool as described hereinbefore, wherein it is understood that the second surface characteristic is not identical to the first surface characteristic according to the invention. It is in particular advantageous that the geometry and dimension of the second treatment surface will allow for the treatment of relatively small skin regions or any skin regions which are difficult to access.

It is further preferred that said skin treatment element comprises a first attachment base and a first tool element incorporating said first surface characteristic, wherein said first tool element is detachably mounted to said first attachment base. According to this preferred embodiment, a separate component, namely the first tool element, is provided which incorporates the first skin treatment surface. This separate component is detachably mounted to a first attachment base which is part of the skin treatment element. As a result, the first tool element may be exchanged and replaced, either providing a different type of skin treatment by a different first surface characteristic, or replacing a first skin treatment surface which does not provide its initial treatment characteristics anymore as a result of wear, contamination or other reasons. The detachable mounting of the first tool element to the first attachment base may be accomplished by a hook-and-loop fastener, any other type of form-locking interaction, an adhesive attachment or the like.

It is particularly preferred that said first tool element has a flat, circular geometry. Such a flat, circular geometry may be attached to a corresponding flat, circular first attachment base, or may be attached to a first attachment base having a different geometry like, e.g., a convex or concave shape, wherein it is understood that the first tool element is flexible to conform to such a curved geometry of the first attachment base.

The skin treatment device may be further improved by adding a plurality of interchangeable first tool elements. It is understood that, according to this embodiment, only one of said first tool elements at a time may be mounted to the first attachment base whilst the other first tool elements may be used to replace this mounted first tool element if it is worn or if another surface characteristic is required.

According to a further preferred embodiment, said skin treatment element comprises a second attachment base and a second tool element incorporating said second surface characteristic, wherein said second tool element is detachably mounted to said second attachment base. According to this embodiment, the second skin treatment surface is incorporated in a second tool element which is detachably mounted to the skin treatment element. The functionalities and advantages of this embodiment are similar to the functionalities and advantages of the embodiment comprising the first attachment base and the first tool element, as discussed hereinbefore.

It is particularly preferred that said second tool element has an annular geometry. In this embodiment, the second tool element may have a rigid and durable structure, wherein the second treatment surface is provided at the outer peripheral surface of the annular second tool element, whilst the inner surface of the annular second tool element serves to transfer the driving force from the second attachment base to the second tool element. The annular second tool element may have a cylindrical form or a conical form or it may have any other form with a curved shape in a longitudinal sectional view comprising the rotational axis. Further, the annular second tool element may have flexible properties to adapt to particular shapes of the second attachment base and to firmly connect to the second attachment base by applying a radially oriented force through circumferential tensioning of the annular second tool element.

It is further preferred that the skin treatment device comprises a plurality of interchangeable second tool elements. In this embodiment, one of said plurality of second tool elements may be mounted to the second attachment base, whilst the others are provided to replace said mounted second tool element when it is worn or when a different skin-treatment functionality is required.

According to a further preferred embodiment, said first skin treatment surface comprises an inner region and a peripheral edge region, wherein said first surface characteristic is not provided at said peripheral edge region. According to this preferred embodiment, the first surface characteristic of the first skin treatment surface is only provided at an inner region of the first skin treatment surface, whilst a peripheral edge region which may preferably be shaped like a circular ring does not have said first surface characteristic. This particular embodiment has the advantage that, using the second skin treatment surface, unintentional contact of the part of the first skin treatment surface, which provides the first surface characteristic, is prevented. Thus, the user may safely apply either the first or the second skin treatment surface and, if doing so, he will treat the skin only with the desired first or second surface characteristic. The peripheral edge region may be rather small in that only a small radial extension of the peripheral edge region is provided, for example the peripheral edge region may have a radial extension of less than 10% of the radius of the first skin treatment surface. Generally, the peripheral edge region extends along the whole circumference of the first treatment surface, i.e. over an angular range of 360° about the rotational axis.

According to a further preferred embodiment, said second skin treatment surface comprises a first region and a second region, said second region being adjacent to said first skin treatment surface, wherein said second surface characteristic is not provided at said second region. In this embodiment, the second skin treatment surface comprises a first region and a second region, which may be designed in such a way as to axially abut each other such that each region extends along the whole circumference of the second skin treatment surface. The second surface characteristic is only provided in the first region such that, during use of the first skin treatment surface, the user cannot unintentionally bring a part of the second skin treatment surface into contact with the skin which comprises the second surface characteristic, thereby effecting a skin treatment by this second surface characteristic. The second region may be shaped like a circular ring and may have a rather small axial extension to accomplish the desired function, for example may axially extend over less than 10% of the overall axial extension of the second skin treatment surface.

According to a further preferred embodiment, said first skin treatment surface has an inner region with an inner first surface characteristic and an outer region with an outer first surface characteristic, which is disposed radially outwardly of said inner region with respect to the rotational axis and which is different from said inner first surface characteristic. According to this embodiment, two or more different properties of the first surface characteristic are provided at the first skin treatment surface. These different properties may, e.g., be represented by different grit sizes of an abrasive surface, a different density of the bristles of a brush-type surface characteristic, or the like. This embodiment addresses the different velocities occurring at the first skin treatment surface due to the different radial distances of the regions of this first skin treatment surface to the rotational axis. Whilst a region which is positioned radially outwardly at the first skin treatment surface will move with a high velocity at a given number of revolutions per minute, a region which is positioned radially inwardly from such radially outward region will move at a lower velocity at the same number of revolutions per minute. Thus, the first skin treatment surface with its axial orientation will produce different velocities, which gradually decrease in a radial direction from the outer periphery to the rotational axis. This is addressed in that at least two different characteristics are provided for the first surface characteristic. For example, the first skin treatment surface may have a fine grit size in an outer region and a coarser grit size in an inner region to compensate for a lower velocity of the inner region compared to the outer region and to have a somewhat balanced treatment efficiency both in the outer and the inner region at a given number of revolutions per minute of the skin treatment element.

According to a further preferred embodiment, said first surface characteristic of said first skin treatment surface changes stepwise or gradually from an inner surface characteristic to an outer surface characteristic in a radial direction with respect to said rotational axis. According to this embodiment, the first surface characteristic is represented by a stepwise or gradually changing characteristic from the outer to the inner region of the first skin treatment surface. Such a stepwise or gradual change of the first surface characteristic will even better compensate for the different velocities occurring at the first skin treatment surface at a given number of revolutions per minute.

According to a still further preferred embodiment, said second skin treatment surface extends over an angular range of 360° about the rotational axis along the circumference of the skin treatment element. According to this embodiment, the second skin treatment surface is formed as a complete ring-shaped surface and thus provides a continuous efficient treatment of the skin when being rotated with a continuous rotational movement.

Generally, the different first and second surface characteristics of the first and the second skin treatment surfaces might be visualized, for example using different colors for the first and second skin treatment surfaces or skin treatment surface regions thereof. This will allow a user to clearly differentiate the surface characteristics and to selectively apply a specific one of the different first and second skin treatment surfaces or skin treatment surface regions thereof.

Still further, a spacing may be present between two skin treatment regions having different surface characteristics. Such a spacing may be embodied as a ring-shaped region having a smooth surface without a surface characteristic which is adapted and intended to apply a skin treatment. This will prevent the undesired or unintended application of a surface characteristic of an adjacent region if another region is intended to be applied by the user.

A further aspect of the invention is a skin treatment element for use in a skin treatment device according to the invention, wherein said skin treatment element is disc-shaped and comprises an attachment portion for coupling said skin treatment element to a drive mechanism for driving said skin treatment element into rotational movement about a rotational axis, wherein said skin treatment element has a first skin treatment surface and a second skin treatment surface, said first skin treatment surface being provided on a main side of the disc-shaped skin treatment element and having an average orientation perpendicular with respect to said rotational axis, said second skin treatment surface being oriented radially with respect to said rotational axis, wherein said first skin treatment surface is formed and intended to effect a skin treatment by a first surface characteristic and said second skin treatment surface is formed to effect a skin treatment by a second surface characteristic, wherein said first surface characteristic and said second surface characteristic are adapted and intended to effect a skin treatment, and wherein said first surface characteristic is different from said second surface characteristic. It is understood that such a skin treatment element is particularly designed by providing a first skin treatment surface and a second skin treatment surface with different first and second surface characteristics. The skin treatment element comprises an attachment portion like an axle, a form-locking coupling member, a shaft, a flange or the like, which allows coupling of the skin treatment element to a drive mechanism which puts the skin treatment element into a rotational movement. The attachment portion is thus adapted to transfer torque from the drive mechanism to the skin treatment element. The skin treatment element may be configured according to the skin treatment element of the skin treatment device described hereinbefore, and it is understood that the skin treatment element may be provided with improvements and variations according to the preferred embodiments of the skin treatment device described hereinbefore.

It shall be understood that the skin treatment device of claim 1 and the skin treatment element of claim 15 have similar and/or identical preferred embodiments, in particular as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF THE EMBODIMENTS

Figure 1:
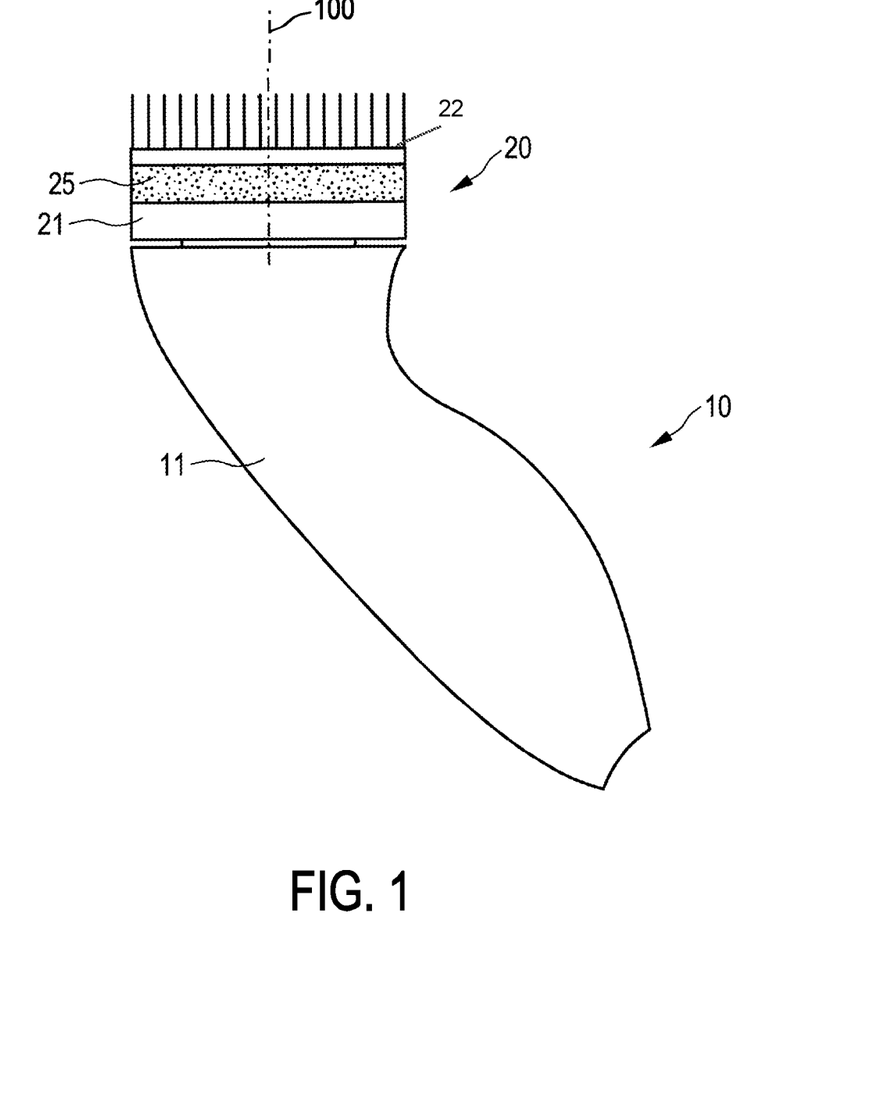
FIG. 1 shows a side view of a skin treatment device according to the invention.

With reference first to FIG. 1, a skin treatment device according to a preferred embodiment comprises a housing 10 and a treatment head 20. The housing 10 comprises a handle section 11 and may incorporate a drive mechanism like an electric motor, a battery, a control unit with a user interface and an interface for charging the battery.

The treatment head 20 comprises a disc-shaped skin treatment element 21. The disc-shaped skin treatment element 21 has an axial first skin treatment surface 22 which is provided on a main side of the disc-shaped skin treatment element 21 is provided with a plurality of bristles to provide a brush-type first surface characteristic. This axial first skin treatment surface 22 has a flat, circular shape and extends perpendicularly to a rotational axis 100. The first skin treatment surface 22 allows a combined cleaning treatment and massage treatment of the skin if the disc-shaped treatment element 21 is put into rotational movement about the rotational axis 100 by the drive mechanism incorporated in the housing 10. The terms "axial" and "radial" are to be understood to refer to the rotational axis 100.

Further, the skin treatment element 21 comprises a radial second skin treatment surface 25 which extends along the circumference of the disc-shaped skin treatment element 21 perpendicularly to a radial direction with respect to the rotation axis 100. This radial second skin treatment surface 25 has an axial width parallel to the rotational axis 100 and extends along the whole periphery of the disc-shaped skin treatment element 21. The outer peripheral surface of the radial second skin treatment surface is coated with abrasive particles to form an abrasive second surface characteristic with a predefined grit size which is constant over the whole circumference and the axial extension of the radial skin treatment surface. It is to be understood that other types of skin treatment surfaces, like brush-type surfaces or polishing surfaces, could be provided at the radial skin treatment surface instead of the abrasive surface.

Figure 2:
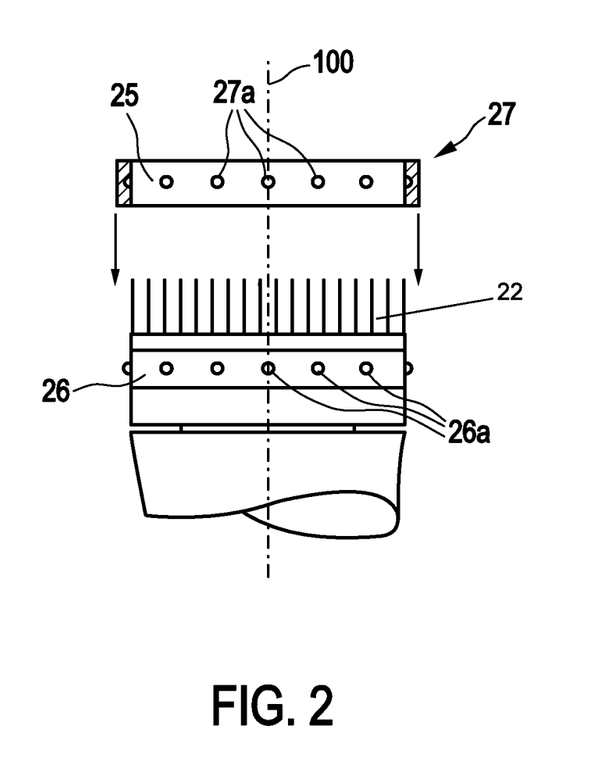
FIG. 2 shows a partially exploded and sectional view of a detail of the skin treatment device of FIG. 1.

As can be seen from FIG. 2, the radial second skin treatment surface 25 is provided on a ring-shaped tool element 27 which can be coupled to an attachment base 26 of the skin treatment element 21. The attachment base 26 has a cylindrical outer geometry with a plurality of protrusions 26a extending in a radial direction with respect to the rotational axis 100. Said protrusions 26a interact in a form-locking manner with corresponding recesses 27a provided at the inner surface of the tool element 27. By virtue of this, a secure and durable coupling of the tool element 27 to the attachment base 26 is reached.

The detachable design of the tool element 27 from the attachment base 26 allows for easy change and replacement of the radial second skin treatment surface 25. By virtue of this, the radial second skin treatment surface may be replaced if it is worn or abraded or contaminated, or it may be exchanged if another surface characteristic like, e.g., a finer or coarser grit size, a brush-type surface characteristic or a polishing surface characteristic is required.

Figure 3:
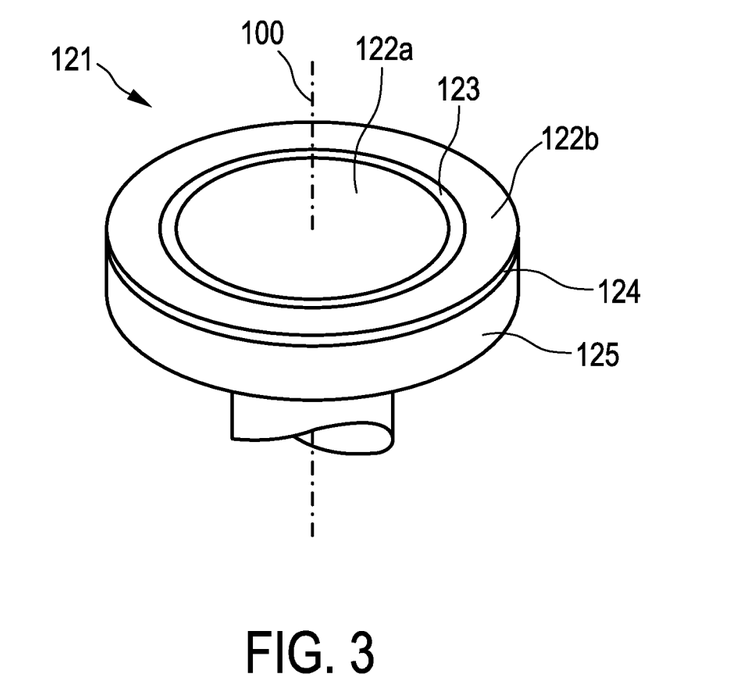
FIG. 3 shows a perspective view of a skin treatment element according to an embodiment of the invention.

With reference to FIG. 3, a skin treatment element 121 may comprise an axial first skin treatment surface having a first inner circular region 122a with a first surface characteristic and a second ring-shaped region 122b with a second surface characteristic that is different from the first surface characteristic. The first surface characteristic may have a relatively coarse grit size like, e.g., an ANSI 120 grit size, whilst the second surface characteristic may have a relatively fine grit size like, e.g., an ANSI 400 grit size, which is functional at relatively high speeds. A ring-shaped space 123 is free of a surface characteristic adapted and intended to effect a skin treatment, and comprises, i.e., a smooth ring arranged between the two regions 122a and 122b to allow selective use of either region 122a or region 122b. Further, a second skin treatment surface 125, having a polishing felt-like structure and being oriented radially with respect to the rotational axis 100, is provided on the circumferential surface of the skin treatment element 121. A ring-shaped free space 124 is positioned at the edge region to prevent unintended contact and application of the first skin treatment surface region 122b when the second skin treatment surface 125 is used.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

Any reference signs in the claims should not be construed as limiting the scope.

The invention claimed is:

1. A skin treatment device, comprising
a housing including a handle section,
a disc-shaped skin treatment element,
a drive mechanism incorporated in said housing, coupled to said skin treatment element, said drive mechanism configured to drive said skin treatment element into rotational movement about a rotational axis,
wherein said skin treatment element has a first skin treatment surface and a second skin treatment surface,
wherein a said first skin treatment surface is provided on a main side of the disc-shaped skin treatment element facing the skin of the user during use having a flat circular shape and an average surface orientation perpendicular with respect to said rotational axis,
wherein said second skin treatment surface is spaced along a radial direction from said rotational axis and is perpendicular with respect to said radial direction and extends along a circumference of the skin treatment element,
wherein said first skin treatment surface is formed and intended to effect a skin treatment by a first surface characteristic and
wherein said second skin treatment surface is formed and intended to effect a skin treatment by a second surface characteristic,
wherein said second skin treatment surface is coupled to an attachment base of the skin treatment element via a plurality of recesses that circumferentially extend around an inner surface of the second treatment surface configured to receive a coupling portion of the attachment base,
wherein said first surface characteristic and said second surface characteristic are adapted and intended to effect a skin treatment, and
wherein said first surface characteristic is different from said second surface characteristic.

2. The skin treatment device according to claim 1, wherein said first surface characteristic is adapted and intended to effect a first type of skin treatment and said second skin treatment surface is adapted and intended to effect a second type of skin treatment different from said first type of skin treatment.

3. The skin treatment device according to claim 2, wherein said first type of skin treatment and said second type of skin treatment are each selected from the group consisting of abrading, polishing, massaging, brushing and cleaning.

4. The skin treatment device according to claim 1, wherein said first surface characteristic is adapted and intended to effect a first type of skin treatment at a first intensity and said second skin treatment surface is adapted and intended to effect said first type of skin treatment at a second intensity different from the said first intensity.

5. The skin treatment device according to claim 1,
wherein said first surface characteristic and/or said second surface characteristic are selected from:
a brush tool,
an abrasive tool with a first grit size,
an abrasive tool with a second grit size which is coarser than the first grit size,
a polishing tool.

6. The skin treatment device according to claim 1,
wherein said skin treatment element comprises a first attachment base and a first tool element incorporating said first surface characteristic, wherein said first tool element is detachably mounted to said first attachment base.

7. The skin treatment device according to claim 6,
comprising a plurality of interchangeable first tool elements.

8. The skin treatment device according to claim 1,
wherein said skin treatment element comprises a second attachment base and a second tool element incorporating said second surface characteristic, wherein said second tool element is detachably mounted to said second attachment base.

9. S treatment device according to claim 8,
wherein said second tool element has an annular geometry.

10. The skin treatment device according to claim 8,
comprising a plurality of interchangeable second tool elements.

11. The skin treatment device according to claim 1,
wherein said first skin treatment surface comprises an inner region and a peripheral edge region, wherein said first surface characteristic is not provided at said peripheral edge region.

12. The skin treatment device according to claim 1,
wherein said second skin treatment surface comprises a first region and a second region, said second region being adjacent to said first skin treatment surface, wherein said second surface characteristic is provided at said first region and not at said second region.

13. The skin treatment device according to claim 1,
wherein said first skin treatment surface has an inner region with an inner first surface characteristic and an outer region with an outer first surface characteristic, which is disposed radially outwardly of said inner region with respect to the rotational axis, wherein said outer first surface characteristic is different from said inner first surface characteristic.

14. The skin treatment device according to claim 1,
wherein said first surface characteristic of said first skin treatment surface changes stepwise from an inner surface characteristic to an outer surface characteristic in a radial direction with respect to said rotational axis.

15. The skin treatment device according to claim 1,
wherein said first surface characteristic of said first skin treatment surface changes gradually from an inner surface characteristic to an outer surface characteristic in a radial direction with respect to said rotational axis.

16. A skin treatment element for use in a skin treatment device,
wherein said skin treatment element is disc-shaped and comprises an attachment portion for coupling said skin treatment element to a drive mechanism for driving said skin treatment element into rotational movement about a rotational axis,
wherein said skin treatment element has a first skin treatment surface and a second skin treatment surface,
said first skin treatment surface being provided on a main side of the disc-shaped skin treatment element and having an average orientation perpendicular with respect to said rotational axis,
wherein said second skin treatment surface is spaced along a radial direction from said rotational axis and is perpendicular with respect to said radial direction and extends along a circumference of the skin treatment element,
wherein said second treatment surface is coupled to an attachment base of the skin treatment element via a plurality of recesses that circumferentially extend around an inner surface of the second treatment surface configured to receive a coupling portion of the attachment base,
wherein said first skin treatment surface is formed and intended to effect a skin treatment by a first surface characteristic and said second skin treatment surface is formed to effect a skin treatment by a second surface characteristic,
wherein said first surface characteristic and said second surface characteristic are adapted and intended to effect a skin treatment, and
wherein said first surface characteristic is different from said second surface characteristic.

* * * * *